United States Patent
Vadelund et al.

(10) Patent No.: US 11,241,386 B2
(45) Date of Patent: Feb. 8, 2022

(54) WOUND SEALING POWDER

(71) Applicant: Biolife, L.L.C, Sarasota, FL (US)

(72) Inventors: Kurt Vadelund, Apollo Beach, FL (US); Talmadge Kelly Keene, Ruskin, FL (US); Mark Travi, Venice, FL (US)

(73) Assignee: Biolife, L.L.C., Sarasota, FL (US)

( * ) Notice: Subject to any disclaimer, the term of this patent is extended or adjusted under 35 U.S.C. 154(b) by 0 days.

(21) Appl. No.: 16/274,406

(22) Filed: Feb. 13, 2019

(65) Prior Publication Data

US 2020/0253874 A1    Aug. 13, 2020

(51) Int. Cl.
| | | |
|---|---|---|
| *A61K 9/14* | (2006.01) | |
| *A61P 7/04* | (2006.01) | |
| *A61P 17/02* | (2006.01) | |
| *A61B 17/12* | (2006.01) | |
| *A61K 9/00* | (2006.01) | |

(52) U.S. Cl.
CPC ............... *A61K 9/14* (2013.01); *A61B 17/12* (2013.01); *A61K 9/0073* (2013.01); *A61P 7/04* (2018.01); *A61P 17/02* (2018.01); *A61B 2017/12004* (2013.01)

(58) Field of Classification Search
CPC . A61K 9/14; A61K 9/0073; A61P 7/04; A61P 17/02; A61B 17/12; A61B 2017/12004
See application file for complete search history.

(56) References Cited

U.S. PATENT DOCUMENTS

| | | | | |
|---|---|---|---|---|
| 4,427,651 A | * | 1/1984 | Stroetmann | A61K 38/4846 424/46 |
| 6,187,347 B1 | * | 2/2001 | Patterson | A61K 31/14 424/484 |
| 8,110,208 B1 | | 2/2012 | Hen | |
| 2013/0149343 A1 | * | 6/2013 | Pesnell | A61P 17/02 424/400 |
| 2014/0330221 A1 | * | 11/2014 | Hen | A61L 24/06 604/290 |
| 2017/0252479 A1 | * | 9/2017 | Ji | A61L 15/26 |

FOREIGN PATENT DOCUMENTS

WO      2014/0153566      9/2014

OTHER PUBLICATIONS

International Search Report and Written Opinion for PCT/US2020/017954, dated Jul. 1, 2020, 15 pages.

* cited by examiner

*Primary Examiner* — Robert A Wax
*Assistant Examiner* — Olga V. Tcherkasskaya
(74) *Attorney, Agent, or Firm* — Nelson Mullins Riley & Scarborough LLP

(57) ABSTRACT

A wound sealing powder, method of making a wound sealing powder, and method of using a wound sealing powder to reduce blood flow from a wound are provided. Specifically, the wound sealing powder utilizes a particulate powder material of an effective amount of an insoluble cation exchange material wherein the majority of the particles in the powder have particle sizes of less than approximately 48 microns.

9 Claims, 5 Drawing Sheets

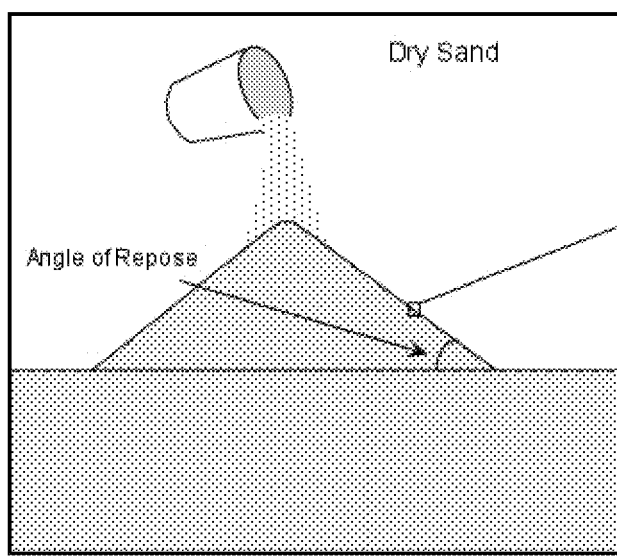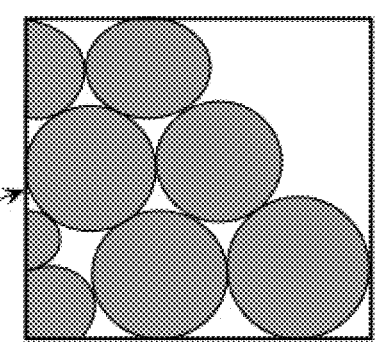
FIGURE 1A                    FIGURE 1B

| Cum % Less than particle size | | | | |
|---|---|---|---|---|
| Particle Size (Micron) | Inv. Process | WS 1.0mm Screen | Test #1 0.35mm Screen | Test #2 0.25mm Screen |
| 1000.0 | 100.0 | 100.0 | 100.0 | 100.0 |
| 750.0 | 100.0 | 100.0 | 100.0 | 100.0 |
| 655.9 | 100.0 | 96.1 | 99.8 | 100.0 |
| 407.8 | 100.0 | 90.4 | 99.5 | 100.0 |
| 321.0 | 100.0 | 81.1 | 81.6 | 100.0 |
| 157.7 | 99.7 | 34.6 | 33.7 | 91.3 |
| 98.1 | 96.1 | 0.4 | 10.6 | 20.3 |
| 77.4 | 93.1 | 0.0 | 7.1 | 10.4 |
| 61.0 | 88.9 | 0.0 | 0.5 | 1.8 |
| 48.0 | 83.3 | 0.0 | 0.0 | 0.6 |
| 38.0 | 67.9 | 0.0 | 0.0 | 0.0 |
| 30.0 | 38.8 | 0.0 | 0.0 | 0.0 |
| 23.5 | 28.9 | 0.0 | 0.0 | 0.0 |
| 18.6 | 24.0 | 0.0 | 0.0 | 0.0 |
| 14.6 | 20.0 | 0.0 | 0.0 | 0.0 |
| 9.1 | 17.4 | 0.0 | 0.0 | 0.0 |
| 5.7 | 7.6 | 0.0 | 0.0 | 0.0 |
| 3.5 | 4.8 | 0.0 | 0.0 | 0.0 |
| 2.2 | 1.3 | 0.0 | 0.0 | 0.0 |
| 0.0 | 0.0 | 0.0 | 0.0 | 0.0 |

FIGURE 2

WOUND SEALING POWDER

FIELD OF THE INVENTION

The present invention relates generally to hemostatic wound sealing topically-applied powders that arrest bleeding, and methods of preparing and using such wound sealing powders.

BACKGROUND OF THE INVENTION

Hemostatic agents are well known in the prior art. For example, Patterson et al., U.S. Pat. No. 6,187,347, which is incorporated herein in its entirety by reference thereto, discloses a free flowing powder to arrest bleeding from a wound by (1) providing a substantially anhydrous compound of a salt ferrate which will hydrate in the presence of blood to produce $Fe^{+++}$ to clot blood and produce oxygen; and (2) applying this compound to the wound for a time sufficient for arresting blood flow, reducing the microbial population, and forming a protective coating over the wound. In one embodiment, a cation exchange material is mixed with the salt ferrate to provide a protective coating over the wound for protection. The salt ferrate provides the oxygen to substantially reduce the level of bacteria, virus and fungus at the wound site. The combination of salt ferrate and an acid cation exchange resin produces $Fe^{+++}$ in a form that allows the iron cation to covalently interact with blood to effect coagulation and create a protective scab over the wound with antimicrobial properties.

Hemostatic agents other than powders are also known in the prior art. For example, U.S. Pat. No. 8,961,479, Hen, et al., which is incorporated herein in its entirety by reference thereto, discloses a tablet form made from a hemostatic powder that may include potassium ferrate and a cation ion exchange resin (sometimes referred to as a hydrogen resin). The powder is pressure formed into a tablet for delivery to a bleeding wound. The tablet improves the rate of adhesion to a bleeding wound surface, and allows a significantly greater and more uniform pressure to be exerted by manual compression of the tablet on the wound site, as compared to that of a thin layer of scattered hemostatic powder. After the seal is formed from the interaction of blood or exudates with the immediate contacting surface of the tablet, the bulk of the unused tablet easily delaminates from the seal making clean-up easier. If the unused portion of the tablet is not removed from the wound site, a reservoir of hemostatic dressing stops further bleeding. The tablet may be applied to any surface orientation and take any shape and thickness possible. Unlike known hemostatic powders, a tablet may be applied to a vertical surface.

In making the wound sealing powder disclosed by Patterson, the cation exchange resin is prepared in the washed hydrogen form, dried at approximately 110° C. for 24 hours and then powdered in a grinder to about 100 mesh size. A 100 mesh powder particle is 149 microns (or 0.149 mm) in diameter.

WoundSeal® topical powder is a commercially available (in 2018) wound sealing product for arresting bleeding from a wound. The current WoundSeal® topical powder consists of a hydrophilic polymer (such as the hydrogen resin referred to above) and potassium ferrate. To use WoundSeal® topical powder, the wound is first cleaned and the powder is poured onto the wound after bleeding resumes because blood must be present for the powder to work.

A flow chart representing the steps in making the 2018 Version of WoundSeal® topical powder is set forth in FIG. 4 and is described as follows. The hydrogen resin may be the hydrogen form of 2% crosslinked, sulfonated polystyrene resin. The hydrogen resin may be available in whole insoluble, generally round, beads having an average particle size of approximately 500 microns in diameter (for purposes of this specification, "diameter" and "particle size", with respect to a particle or particles, are synonymous), or alternatively, the resin may be available in, or ground into, much finer fragments averaging in size from 80 microns to 200 microns in diameter.

The hydrogen resin (with Purolite CT122 available from Purolite Corporation of Bala Cynwyd, Pa. being a suitable such resin) is initially dried, for example, in an oven at a temperature of approximately 100° C. to 110° C. for an average of 12½ days, depending on the ambient moisture. The goal of drying the resin is to achieve a moisture content of 3% or less, and typically a moisture content of approximately 1%. During the drying process, the particle size of the resin is typically reduced due to the dehydration of the water molecules from the resin. Drying the resin reduces the ability for the resin to transport or exchange protons, and, therefore, a dry resin is rendered generally inert. It is necessary to dry the resin to a certain degree if the resin is to be mixed with another dry proton acceptor.

The ferrate may be purchased or may be produced by mixing iron oxide with an oxidizing agent and then heating, until ferrate cakes are produced. When ferrate cakes are used, the cake is broken into smaller pieces, typically manually or with known machinery, and then a knife grinder, or other known suitable device, is used to break up the cake. In a typical instance, a knife grinder with a 2 mm screen may be used. This breaking process results in the ferrate having a particle size of 2 mm or less in diameter.

WoundSeal® topical powder is typically made from an approximately 1:7 weight mixture of potassium ferrate: hydrogen resin, although weight mixtures ranging from 1:3 to 1:12 will adequately arrest bleeding, depending on the particular application. In one embodiment, the ferrate (after breaking) and the resin (after drying) are mixed and then ground in a Turbo Mill, which is a rotor mill style grinder that utilizes a high speed rotor contained in a grinding chamber with a screen that reduces the particle size through impact with the rotor and screen. The particle size is controlled via rotor speed and screen opening size. Based on the size of the unground beads and the size of the openings in the grinding screen, a fraction of the unground (whole) bead will pass through the grinding process and there is typically no post-grind screening process.

The Turbo Mill has a continuous feed into the mill, and a continuous flow of particles out of the mill of particles that have passed through the control screen. The screen used in this embodiment is a 1 mm screen and the mill is run at a production speed of 20 kg/hr to 25 kg/hr to obtain the WoundSeal® topical powder. After production, the powder is stored in closed containers, such as plastic tubs, in order to deter re-hydration until the powder can be packaged in consumer-ready packaging for sale.

Although WoundSeal® topical powder is a reliable, hemostatic product, users have indicated a need for certain improvements to the product. First, users have noted that the color of the product is less than desirable, often described as appearing "dirty" or having the color of dirt. This color contrasts greatly with certain skin coloration and is noticeable when in use. Second, users have noted that achieving adherence to an angled or near vertical skin surface is difficult. The powder is readily applied to horizontal surfaces, such as when the patient's wound is in a near horizontal position. The unground portion of resin (the remaining generally round beads) causes the powder to spread out relatively evenly on a completely horizontal surface. However, when the powder is applied to a more vertical surface, such as the patient's face or neck area, or a curved or irregular surface, such as the patient's arm, the powder 2018 version of WoundSeal® topical powder tends to roll off. Some of the powder is wasted as it falls off and fails to achieve cohesion to other particles or adhesion with the more vertical or rounded skin surface.

Thus, there is a need to have an effective wound-sealing powder that exhibits more acceptable color to consumers and that allows for less waste, more adhesion of the powder onto more vertical surfaces of the body, and greater cohesiveness of the powder. The present invention attempts to fulfill those long-felt needs.

The foregoing examples of the related art and limitations related thereto are intended to be illustrative and not exclusive. Other limitations of the related art will become apparent to those skilled in the art upon a reading of the specification and a study of the drawings.

SUMMARY OF THE INVENTION

Briefly, the present invention is directed, in an embodiment, to a composition useful as a wound sealing powder that comprises a particulate powder consisting essentially of a substantially anhydrous salt ferrate compound combined with an effective amount of an insoluble cation exchange material wherein the particle size distribution range of the particles in the powder is 160 microns or less.

In another embodiment, the invention is directed to a wound sealing composition comprising a particulate powder consisting essentially of a substantially anhydrous salt ferrate compound combined with an effective amount of an insoluble cation exchange material wherein the majority of the particles in the powder have particle sizes of less than approximately 48 microns.

In another embodiment, the invention is directed to a wound sealing composition comprising a particulate powder consisting essentially of a substantially anhydrous salt ferrate compound combined with an effective amount of an insoluble cation exchange material wherein the powder contains essentially no particles having a particle size of 158 microns or more In another embodiment, the invention is directed to a method of making a particulate powder for a wound sealing composition wherein the powder consists essentially of a substantially anhydrous salt ferrate compound combined with an effective amount of an insoluble cation exchange material wherein the powder contains essentially no particles having a particle size of 158 microns or more, the method comprising steps of drying an insoluble cation exchange material to a moisture content of approximately 3% or less; mixing a substantially anhydrous salt ferrate compound having an average particle size of 2 mm or less with the cation exchange material at a weight ratio of approximately 1 to 2, ferrate to cation exchange material; providing the dried cation exchange material at an average particle size of less than about 70; blending the mixed 1:2 ferrate:cation exchange material with the dried cation exchange material having an average particle size of less than about 70 microns to obtain an approximate 1 to 7 weight mixture of ferrate to cation exchange material.

In yet another embodiment, the invention is directed to a method of arresting or reducing the blood flow from a wound on a patient having a blood-letting wound comprising the steps of applying a wound sealing composition comprising a particulate powder consisting essentially of a substantially anhydrous salt ferrate compound combined with an effective amount of an insoluble cation exchange material wherein the majority of the particles in the powder have particle sizes of less than approximately 48 microns and allowing a seal to form over the wound so that blood flow from the wound is reduced.

In another embodiment, the invention is directed to a wound sealing composition comprising a particulate powder consisting essentially of a ground insoluble cation exchange material wherein the particle size distribution range of the particles in the powder is 160 microns or less. And, in another embodiment, the invention is directed to a wound sealing composition comprising a particulate powder consisting essentially of a ground insoluble cation exchange material wherein the majority of the particles in the powder have particle sizes of less than approximately 48 microns.

In yet another embodiment, the invention is directed to a wound sealing composition comprising a particulate powder consisting essentially of an insoluble cation exchange material wherein the particle size distribution range of the particles in the powder is 160 microns or less and the moisture content of the powder is 20% or less. And, in yet another embodiment, the invention is directed to a particulate powder consisting essentially of a ground insoluble cation exchange material wherein the majority of the particles in the powder have particle sizes of less than approximately 48 microns and the moisture content of the powder is 20% or less.

BRIEF DESCRIPTION OF THE DRAWINGS

FIG. 1A illustrates the angle of repose for the powder particles of the present invention.

FIG. 1B illustrates a magnified portion showing the powder particles of FIG. 1A.

FIG. 2 illustrates the particle size distribution of the inventive wound sealing powder ("Inv. Process") versus the particle size distribution of the 2018 Version of Wound-Seal® ("WS") topical powder and two test powders (Test #1, Test #2) in table form.

DETAILED DESCRIPTION OF PREFERRED EMBODIMENTS

Figure 3:
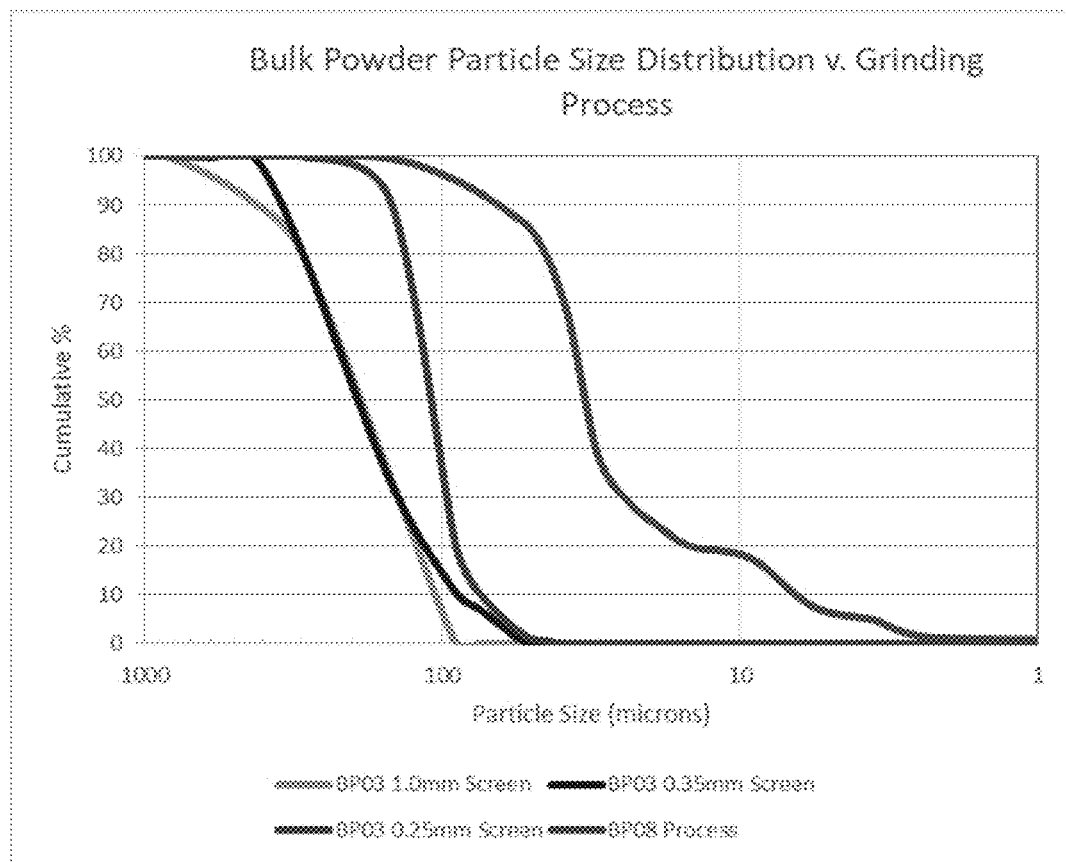
FIG. 3 illustrates the same particle size distribution of FIG. 2 in the alternate graph form ("BP03 1.0 mm" is the 2018 Version of WoundSeal® topical powder; "BP03 0.35 mm" and "BP03 0.25 mm" are Test #1 and Test #2), and "BP08 Process" is the topical powder of the present invention).
Figure 4:
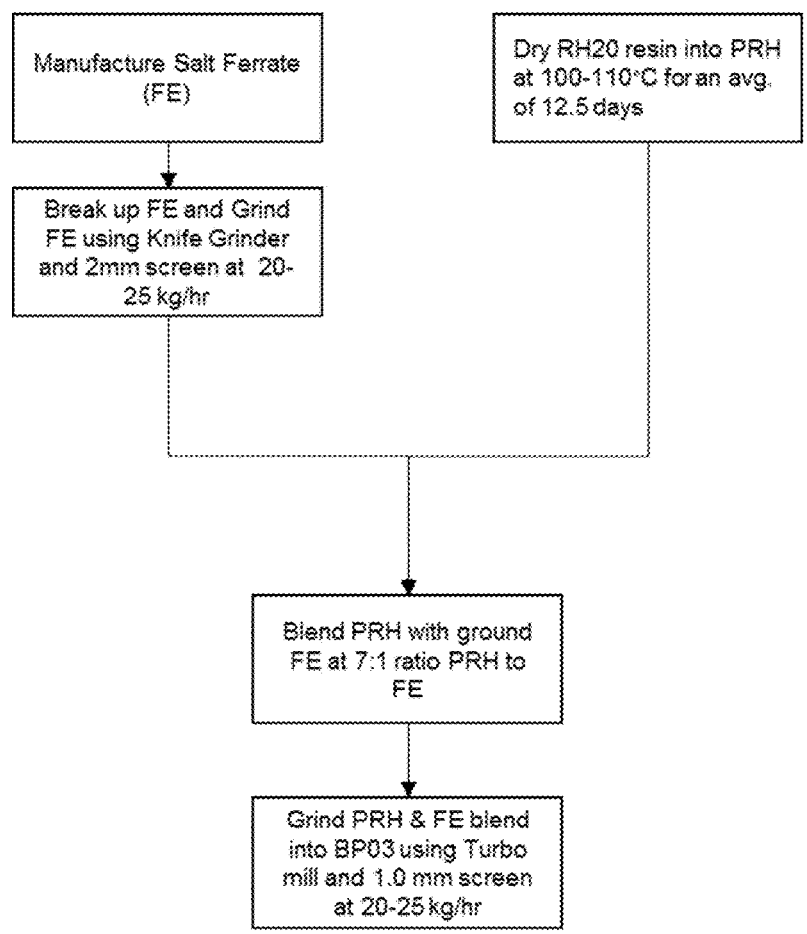
FIG. 4 illustrates the process of making the 2018 Version of WoundSeal® topical powder in flow chart form.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Ion exchange resins are typically prepared as spheres with a particle size that typically range from less than 10 microns for high pressure liquid chromatography, from 40 microns to 250 microns for ingestible drug delivery resins, and from 300 microns to 1200 microns for some industrial applications. These sizes are fully hydrated sizes, because the vast majority of all resin is used in the fully hydrated state. Resin, as manufactured, has an average size (diameter) with a Gaussian distribution, and the variation of bead size is based on the manufacturing process. The resin can then be further sized by grinding and/or fractional screening to acquire the proper size to suit an application. For drug delivery systems, similar sizes with a narrow Gaussian distribution are needed to ensure consistent delivery. For industrial liquid processing applications using an ion exchange resin bed, if the size distribution is too broad, the bead stacking will be affected and flow characteristics through the bed will be impeded, resulting in high pressure drops across the column of the ion exchange resin. The pressure drop increase occurs because the smaller particles can fit into the spaces between the larger particles, thus impeding liquid flow.

When a dry strong acid cation resin in hydrogen form (hereinafter SACR-H) is applied to blood, the SACR-H floats on the blood surface, rapidly absorbing liquid from the blood. The pores of the resin are too small to absorb blood solids or large proteins. This rapid absorption of the liquid, while excluding the blood solids, causes the solids to stack up beneath the SACR-H. These solids continue to stack until the liquid can no longer be transferred through the barrier of blood cells that have been formed. If this barrier is pushed into contact with a surface it will adhere to the surface, due to the natural glue-like nature of dried blood. If this surface is a bleeding wound, then the barrier will adhere to the wound site and stop further bleeding.

If dry, essentially round, SACR-H beads are poured onto a bleeding site, the beads that contact the blood will adhere to the blood, but additional beads will simply roll off the wound site, particularly if the wound site is not positioned horizontally, but is instead more vertical such as the neck, chest, or head region of a standing patient. This is also observed where the wound site is on a curved portion of the body, such as an arm, finger, or toe. A monolayer of beads that may adhere to such rounded or more vertically-positioned skin surfaces will provide less adequate absorption capacity and a reduced ability to stop a bleeding wound without multiple applications. Several layers may be needed to absorb sufficient liquid from the blood to create a barrier of sufficient strength to stop bleeding from a wound.

The inventors have found that, in order to solve this need to adhere more of the powder at the wound site, the resin may be ground to smaller particles so that the angle of repose when the powder is applied is increased because the frictional contact area from particle to particle (i.e., cohesion between particles) is increased. Typically, the amount of unground, relatively round beads remaining in the inventive powder will be 5% or less in the final powder. These effects are shown in FIG. 1A and, in magnified form, 1B.

This increase in angle of repose allows for multiple layers of powder to remain over a bleeding wound while reducing the amount of material that readily falls off the wound site during application. In addition to an increase in angle of repose, the increased angularity also allows the product to adhere better to a more inclined or curved wound surfaces. The angle of repose obtained with the present inventive wound sealing powder is typically in the range of 40° to 50° as compared to the angle of repose typically found with the currently available WoundSeal® topical powder which ranges from 25° to 30°. The newly invented powder has both better cohesion between particles and better adhesion to the patient or wound site.

SACR-H has a negative pKa (indicative of a strong acid), similar to that of hydrochloric acid. When applied to blood, a portion of the hydrogen atoms attached to the resin backbone are neutralized, but the remaining hydrogen atoms on the resin backbone have anti-bacterial properties. Due to stacking properties, if whole beads are applied and adhered to a blood barrier above a wound, there will be spaces between the beads large enough for bacterial intrusion versus the tightly-spaced packing created by a more finely ground SACR-H product.

However, a powder that is ground too finely could create a small dust cloud when applied. In addition, if the particles are too small, they may also create lung inhalation issues. To overcome some of these traits, in certain embodiments, additional coagulating agents or wound healing agents may be combined with the SACR-H.

To fulfill the long-felt need of increasing the adhesion of the powder to all skin surfaces by increasing the cohesion amongst the particles, appropriate starting materials with the appropriate grinding and screening methodologies are employed. Screening out the "too low" and "too high" fractions or particle sizes results in a narrower and lower range of particle size distribution allowed by the present invention in order to provide the required adhesiveness to the wound.

In the present invention, SACR-H used in the hemostatic powder is purchased from a supplier as spherical beads ranging in size from 150 microns to 1000 microns after drying to a moisture content of less than about 3% (although, typical drying results in a moisture content of approximately 1% or less). The dried SACR-H resin beads are then ground to a suitable particle size distribution to disperse onto a wound to result in a good adhesion to reduce the amount of powder that fails to adhere to the wound and simply falls off the skin surface during application.

Another benefit of the use of a SACR-H with a smaller particle size distribution that meets another of the long-felt needs is that the resulting powder becomes lighter in color.

Unlike the 2018 version of WoundSeal® topical powder, which is typically a dark amber brown color, the present inventive wound sealing powder exhibits a color that more buff tan and which more closely matches a Caucasian skin color. This more favorable color has major marketing implications as an acceptable product in that the more uniform buff tan color is more consistent and is not perceived as being a "dirty brown" powder. The more finely ground powder has a color and texture more similar to that of a cosmetic material.

Example 1

Figure 5:
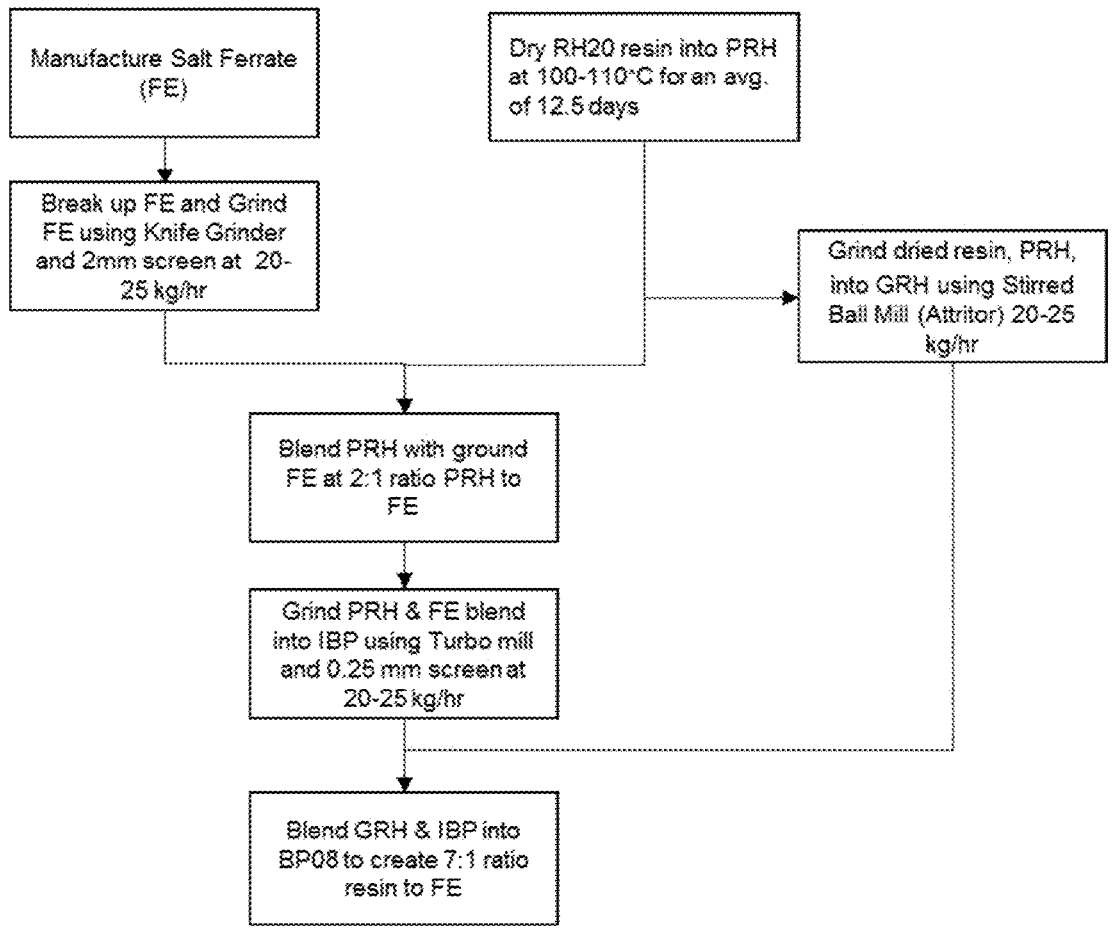
FIG. 5 illustrates the process of making the inventive wound sealing powder in flow chart form.

In this example, a wound sealing powder that exhibits better adhesion and cohesion properties and a more acceptable uniform color than the 2018 version of WoundSeal® topical powder is made as shown in the flow chart set forth in FIG. 5 and as described below.

One hydrogen resin that may be employed is Purolite CT122 available from Purolite Corporation of Bala Cynwyd, Pa. However, it will be understood by one of ordinary skill in the art that other hydrophilic cationic resins in hydrogen form may be used. The particular resin employed in one embodiment has a particle size distribution of: 1) up to 10% of greater than 1400 microns; 2) up to 5% of less than 850 microns; and 3) up to 2% of less than 425 microns, with the primary particle size range being from 850 microns to 1400 microns.

Initially, the resin is dried, for example, in a static dryer such as an oven at a temperature of approximately 100° C. to 110° C. for an average of 12½ days. The variation of drying time may be depending on the drying conditions, including but not limited to ambient moisture. The goal of drying the resin is to achieve a moisture content of 3% or less, and typically a moisture content of approximately 1%, this drying process converts the resin from an active proton exchange state to a relatively inactive proton exchange state until rehydrated. During the drying process, the particle size of the resin is typically reduced due to the dehydration of the water molecules from the resin.

The ferrate may be purchased or may be produced by cooking iron oxide with an oxidizing agent and then heating, until ferrate cakes are produced. When ferrate cakes are used, the cake is broken into smaller pieces, typically manually or with known machinery, and then a knife grinder, or other known suitable device, is used to break up the cake. In a typical instance, a knife grinder with a 2 mm screen may be used. This breaking process results in the ferrate having a particle size of 2 mm or less in diameter.

The first step in the powder mixing process is to mix the screened ferrate (2 mm screen) with dried resin at a ratio of 1:2 ferrate:hydrogen resin. This mixture may then be subjected to grinding in a Turbo Mill (described above) using a 0.25 mm screen at a production rate, for example, of 20 to 25 kg/hr to obtain an intermediary product.

The next step is to grind dried hydrogen resin alone in an Attritor Mill at a production rate, for example, of 20 kg/hr to 25 kg/hr. Unlike the Turbo Mill, an Attritor Mill is a stirred ball mill that uses larger hard stainless steel spheres (for example, 9 mm 10 mm in diameter) agitated by rotating agitator arms to crush smaller and softer material. The grinding action is caused by the impact of the stainless steel spheres, agitator arms, and sides of the grinding tank. Particle size is controlled via agitator arm speed, size of grinding media, and grinding time. In one particular embodiment, the Attritor Mill is used to grind the dried hydrogen resin to an average particle size of approximately 40 microns (but one of ordinary skill in the art will appreciate that average particle sizes of up to 70 microns would be suitable for the present invention).

This 40 micron-sized dried resin is then blended with the 1:2 ferrate:hydrogen resin mixture to obtain an approximately 1:7 weight mixture of ferrate:hydrogen resin, although weight mixtures ranging from 1:3 to 1:12 will adequately arrest bleeding, depending on the particular application. After blending, the powder is stored in closed containers, such as plastic tubs, in order to deter re-hydration until the powder can be packaged in consumer-ready packaging for sale.

FIG. 2 (table form) illustrates the particle size distributions of the inventive wound sealing powder ("Inv. Process") versus the particle size distribution of the 2018 Version of WoundSeal® ("WS") topical powder and two test powders (Test #1, Test #2). Likewise, FIG. 3 (graph form) illustrates the same particle size distribution of FIG. 2 ("BP03 1.0 mm" is the 2018 Version of WoundSeal® topical powder; "BP03 0.35 mm" and "BP03 0.25 mm" are Test #1 and Test #2), and "BP08 Process" is the inventive wound sealing powder).

As shown in FIG. 2, wound sealing powders consisting of the ferrate and resin mixture, including WoundSeal® topical powder as it existed in 2018 and before and two test wound sealing powders that are not commercially available and that heretofore have not been disclosed, demonstrated a particle size distribution ranging from approximately 100 microns to approximately 700 microns when employing a 1.0 mm screen (WoundSeal® topical powder 2018 Version); from approximately 60 microns to approximately 700 microns when employing a 0.35 mm screen (Test #1); and from approximately 60 microns to approximately 200-300 microns when employing a 0.25 mm screen (Test #2). In contrast, the present inventive powder and process results in a particle size distribution ranging from approximately 2 microns to 158 microns.

In the wound sealing powders screened with a 1.0 mm screen (WoundSeal® topical powder 2018 Version) or 0.35 screen (Test #1), the majority of particles (approximately 65%) had a particle size of more than approximately 158 microns; and screened with a 0.25 mm screen (Test #2), the majority of particles (approximately 80%) had a particle size of more than approximately 98 microns. In contrast, the inventive wound sealing powder had essentially no particle sizes (0.3%) of more than approximately 158 microns and only a small minority (3.9%) of particles more than approximately 98 microns. For purposes of this specification "essentially no particles sizes" means 10% or less of the particles have the stated diameter.

In further comparison, none of the wound sealing powders analyzed had particle sizes less than about 48 microns but the inventive wound sealing powder had an overwhelming majority of particles sized (83.3%) less than 48 microns.

As shown in FIG. 3, the median particle size for the tested wound sealing powders screened with 1.0 mm (WoundSeal® topical powder 2018 Version) and 0.35 mm (Test #1) screens was approximately 190 microns and for those screened with 0.25 mm (Test #2) screens was approximately 110 microns. In contrast, the median particle size for the inventive wound sealing powder is approximately 55 microns.

The comparative bulk densities of the products are approximately 0.75 g/cc for the 2018 Version of WoundSeal® topical powder and approximately 0.60 g/cc for the inventive wound sealing composition.

UNEXPECTED RESULTS

The inventive wound sealing powder was found to exhibit several unexpected results when applied to a wound in the same manner as the 2018 Version of the WoundSeal® topical powder.

First, one of ordinary skill in the art would expect a finer ground power due to the migration activity of smaller particles. However, during end-user testing in a hospital setting, the finer-ground inventive powder was found to be less messy than the 2018 version of WoundSeal® topical powder.

Second, the color of the powder was lighter and more appealing to the hospital staff. The new inventive powder looks more like makeup, than dirt.

It was also unexpectedly found that the inventive more uniform and more finely ground powder, when compressed into a tablet, exhibits a reduction in deterioration rate caused by atmospherically-absorbed moisture. A tablet made with from the powder used to make the 2018 version of WoundSeal® topical powder deteriorates to the point that it cannot be properly handled and packaged if exposed to typical atmospheric conditions.

Third, the more uniformly ground particles of the present invention expand at a more similar rate, thus unexpectedly keeping the powder in better and longer position on a vascular catheter site as compared to the larger powder particles of the 2018 version of WoundSeal® topical powder.

Another unexpected result of the newly invented powder is that when the powder is compressed into a tablet the reduction in overall bulk expansion of the mass of particle create a table with more structural integrity as it absorbs moisture from the surrounding air. The dried material will uptake water from the surrounding air and expand. Tablets created with the finer powder, nearly void of spherical particles, are more uniform in appearance, and the resulting tablets are harder than tablets created with the 2018 powder under the same compression force.

In addition to the tablets being harder and stronger, the tablets can be manufactured thinner. This reduction in heights will reduce the likelihood for a compressed tablet to create a pressure ulcer in a patient. The minimum height limit for the 2018 powder is thicker than the newly invented powder due to the number of round particles that will not tightly interlock. Even with the tightly interlocking of the newly invented powder tablets, and lack of expansion in air, the tablets will still delaminate upon application to a bodily liquid. The difference in expansion characteristics in air and upon application to a bodily liquid is due to the difference in relative expansion within the tablet.

In addition, the dried blood barrier that is created between the powder and the wound also lessens interaction between the wound and any pigments that are added to affect the final color of the product, including entrapment as the wound heals. These and other unexpected results demonstrate the patentability of the presently claimed wound sealing powder.

Finally, it is to be understood that the described grinding and formation processes above could be utilized to form a wound sealing powder consisting of only the hydrogen resin (without the ferrate or pigment), and without the 3% moistures level constraint, as described in U.S. patent application Ser. No. 14/147,143, which is incorporated by reference herein in its entirety.

All references cited in this specification, including without limitation, all papers, publications, patents, patent applications, provisional patent applications, presentations, texts, reports, manuscripts, brochures, books, internet postings, journal articles, and/or periodicals are hereby incorporated by reference into this specification in their entireties, including all figures and tables, to the extent they are not inconsistent with the explicit teachings of this specification. The discussion of the references herein is intended merely to summarize the assertions made by their authors and no admission is made that any reference constitutes prior art. Applicants reserve the right to challenge the accuracy and pertinence of the cited references.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the versions contained therein.

What is claimed is:

1. A wound sealing composition comprising a particulate powder consisting essentially of mixture of a substantially anhydrous salt ferrate compound and an effective amount of an insoluble cation exchange material, wherein at least 90% of the particles in the powder have a particle size of 77.4 microns or less.

2. A wound sealing composition comprising a particulate powder consisting essentially of mixture of a substantially anhydrous salt ferrate compound and an effective amount of an insoluble cation exchange material, wherein the majority of the particles in the powder have particle sizes of less than approximately 48 microns.

3. The wound sealing composition of claim 2, wherein at least 60% of the particles in the powder have particle sizes of less than approximately 48 microns.

4. The wound sealing composition of claim 2, wherein at least 70% of the particles in the powder have particle sizes of less than approximately 48 microns.

5. The wound sealing composition of claim 2, wherein at least 75% of the particles in the powder have particle sizes of less than approximately 48 microns.

6. The wound sealing composition of claim 2, wherein at least 80% of the particles in the powder have particle sizes of less than approximately 48 microns.

7. The wound sealing composition of claim 2, wherein at least 83% of the particles in the powder have particle sizes of less than approximately 48 microns.

8. The wound sealing composition of claim 2 further comprising one or more components chosen from the following: hemostatic salt, cosmetic pigment, and/or antimicrobial, wherein the one or more components are in particulate form, and wherein the majority of the particles of the one or more components have particle sizes of less than approximately 48 microns.

9. The wound sealing composition of claim 2, wherein the composition comprises at least 75% by weight insoluble cation exchange material.

\* \* \* \* \*

UNITED STATES PATENT AND TRADEMARK OFFICE
CERTIFICATE OF CORRECTION

| | | |
|---|---|---|
| PATENT NO. | : 11,241,386 B2 | |
| APPLICATION NO. | : 16/274406 | |
| DATED | : February 8, 2022 | |
| INVENTOR(S) | : Kurt Vadelund, Talmadge Kelly Keene and Mark Travi | |

It is certified that error appears in the above-identified patent and that said Letters Patent is hereby corrected as shown below:

In the Claims

In Column 10, Line 64, Claim 9, please change "weight insoluble" to --weight of insoluble--

Signed and Sealed this
Nineteenth Day of July, 2022

Katherine Kelly Vidal
*Director of the United States Patent and Trademark Office*